United States Patent [19]

Mechlenburg

[11] Patent Number: 4,616,501
[45] Date of Patent: Oct. 14, 1986

[54] SYSTEM FOR DETERMINING GAS CONCENTRATION

[75] Inventor: Douglas M. Mechlenburg, Erie, Pa.

[73] Assignee: American Sterilizer Company, Erie, Pa.

[21] Appl. No.: 726,136

[22] Filed: Apr. 23, 1985

[51] Int. Cl.4 .......................................... G01N 29/02
[52] U.S. Cl. ...................................................... 73/24
[58] Field of Search ...................................... 73/24, 23

[56] References Cited

U.S. PATENT DOCUMENTS 3,981,176  9/1976  Jacobs ........................................ 73/24
4,520,654  6/1985  Terhune ...................................... 73/24

Primary Examiner—Stephen A. Kreitman
Attorney, Agent, or Firm—Robert D. Yeager

[57] ABSTRACT

A system employs ultrasound to determine the concentration of gases present within a chamber. The system causes ultrasound to propagate through the chamber at each of at least two operating frequencies. The amplitude of the ultrasound at a predetermined point within the chamber is recorded for each operating frequency to form a set of measured amplitudes. The set of measured amplitudes is compared to a mathematical model developed experimentally that expresses the amplitude response of the system.

3 Claims, 6 Drawing Figures

4,616,501

SYSTEM FOR DETERMINING GAS CONCENTRATION

BACKGROUND OF THE INVENTION

1. Field of the Invention

The present invention pertains to devices for determining the concentration of gas and, more particularly, to a system that employs ultrasound to determine gas concentration.

2. Description of the Prior Art

Ethylene oxide ("EtO") is commonly used as the sterilizing agent in gas sterilizers. As the sterilization cycle proceeds, it is necessary to monitor the concentration of EtO within the sterilization chamber to ensure that the proper sterilization sequence is occurring and to correct any departures from the standard sterilization cycle. Further, the effectiveness of EtO as a sterilizing agent is optimized, and, hence, the time consumed by the sterilization cycle is minimized, when the relative humidity within the sterilization chamber is maintained between 20 and 40 percent. Therefore, there exists the need for a device that can accurately measure the concentration of EtO and water vapor within a sterilization chamber.

Several types of systems for measuring gas concentration are known. Gas chromatography systems offer good sensitivity and reliability, but are relatively expensive. Infrared spectroscopy provides low sensitivity, low dynamic range and requires a relatively high degree of maintenance. Solid-state sensors are highly sensitive and relatively inexpensive, but cannot measure the concentration of a single gas within a chamber that contains multiple gases.

Therefore, there exists the need for a system for determining the concentration of each of multiple gases present within a chamber that is both highly sensitive and relatively inexpensive.

SUMMARY OF THE INVENTION

The present invention provides a system that gives an indication of the concentration of at least one gas present within a chamber. The system includes apparatus for causing mechanical radiant energy, such as sound or ultrasound, to propagate through the chamber at at least two operating frequencies. The system also includes apparatus for measuring the amplitude of the propagating mechanical radiant energy at each operating frequency at a predetermined point within the chamber. The system also includes apparatus for using the measured amplitudes and information pertaining to the amplitude of mechanical radiant energy propagating at each propagating frequency through the at least one gas at each of a set of known concentrations to determine the concentration of the at least one gas present in the chamber.

BRIEF DESCRIPTION OF THE DRAWINGS

The following detailed description of the preferred embodiments can be understood better if reference is made to the drawings, in which.

DETAILED DESCRIPTION OF THE PREFERRED EMBODIMENTS

METHODOLOGY

Figure 3:
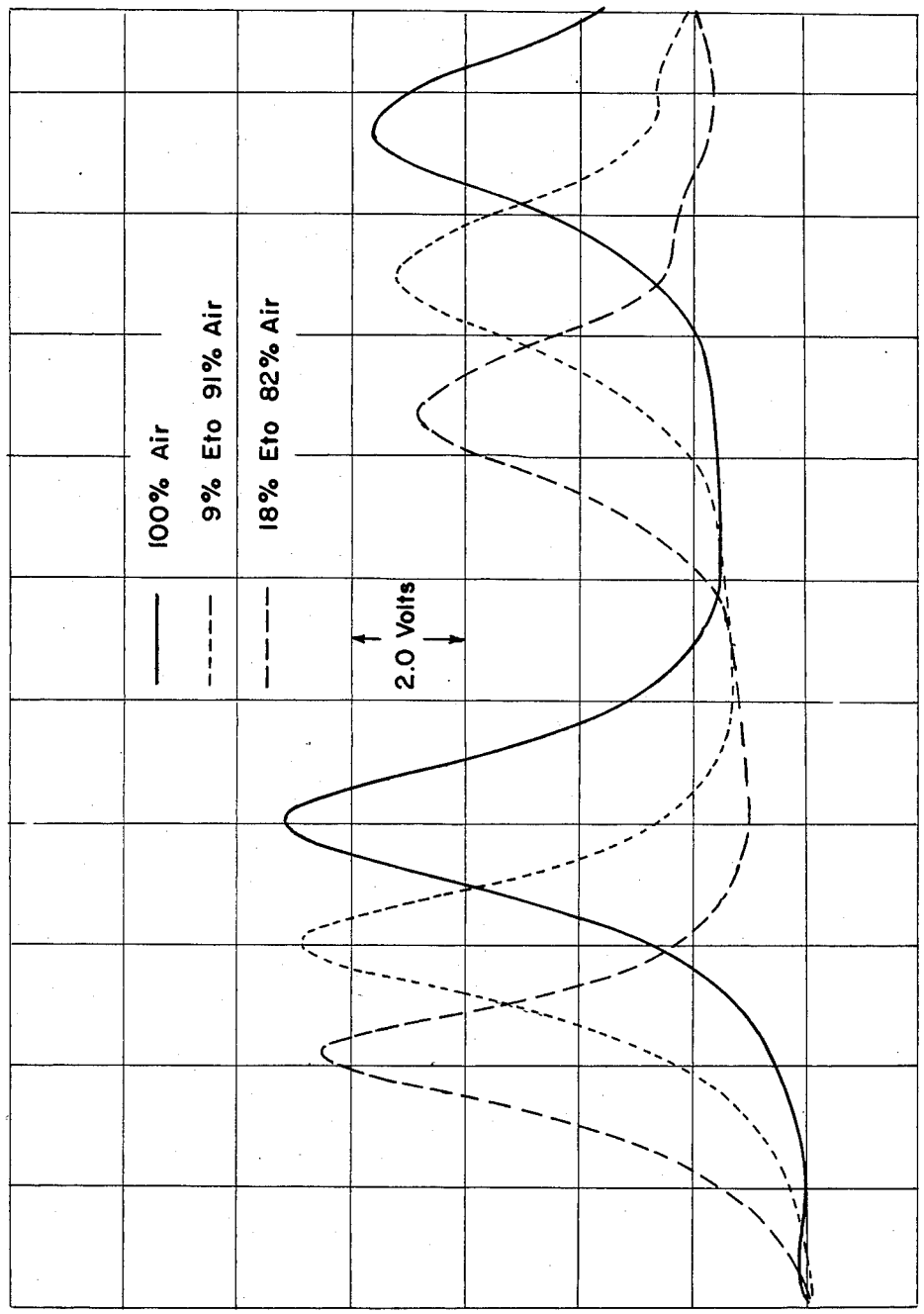
FIG. 3 is a graphical representation of the variation of the amplitude of ultrasound propagating through a chamber containing EtO and air in various concentrations.
Figure 4:
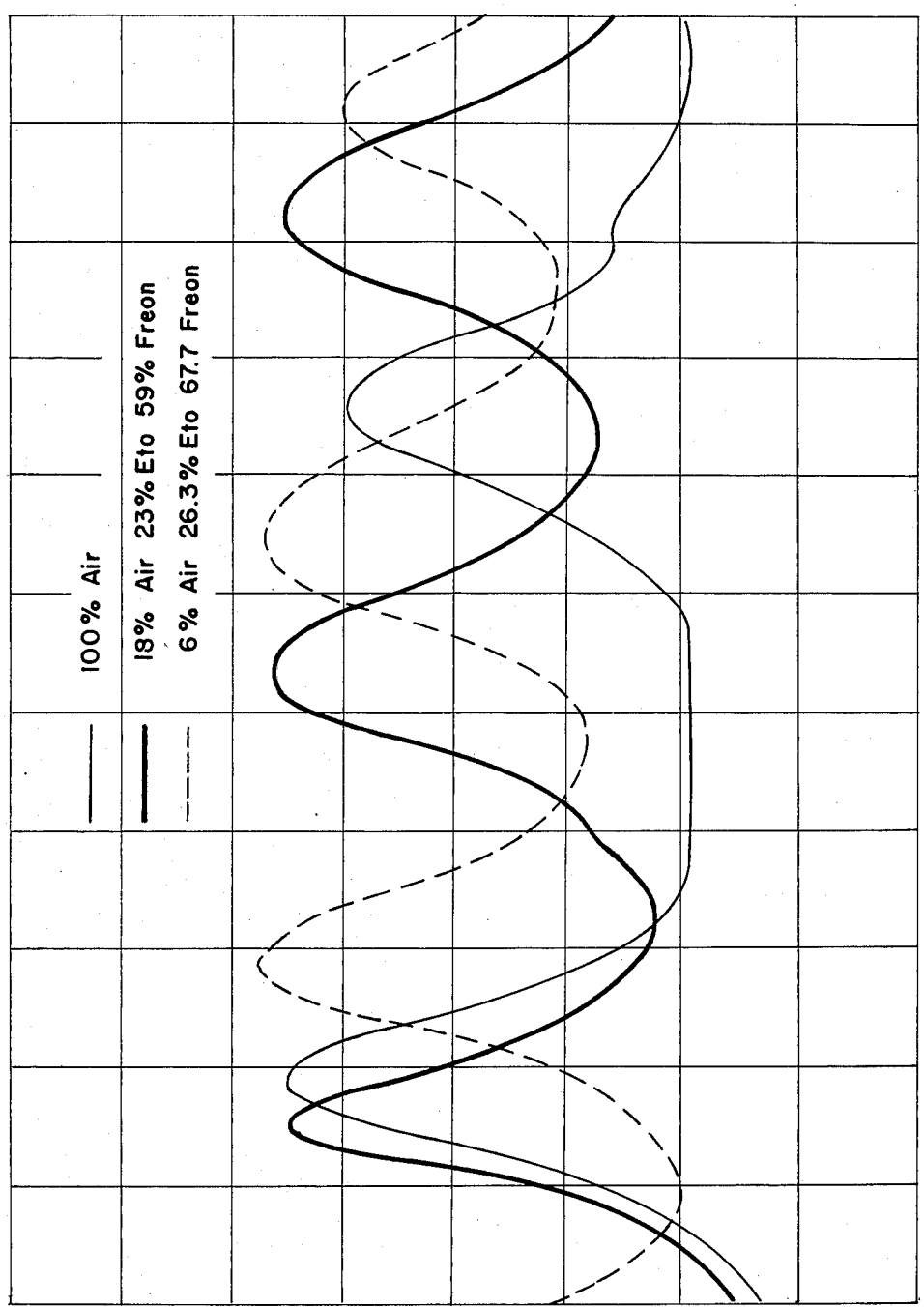
FIG. 4 is a graphical representation of the variation of the amplitude of ultrasound propagating through a chamber containing air, EtO and Freon in various concentrations.
Figure 5:
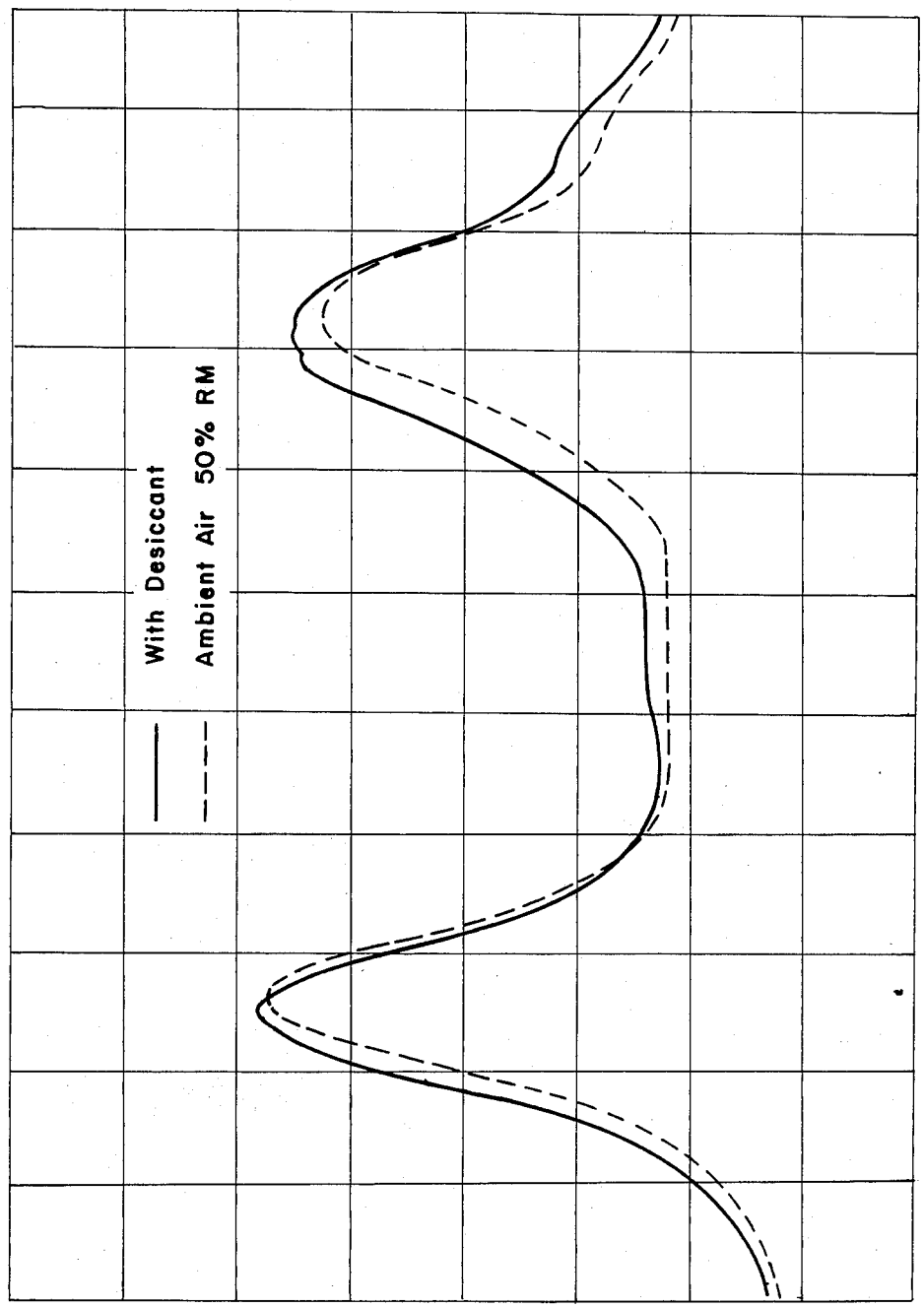
FIG. 5 is a graphical representation of the variation of the amplitude of ultrasound propagating through a chamber containing water vapor in various concentrations.

System 10, which is the preferred embodiment of the present invention, employs ultrasound to determine gas concentration. The amplitude of ultrasound propagating through various gases in various concentrations is shown in FIGS. 3, 4 and 5. As can be seen from FIGS. 3 through 5, the amplitude of ultrasound energy propagating through gases present in predetermined concentrations varies with frequency. That characteristic of ultrasound is employed by the present invention to determine the concentration of gases present in a chamber.

System 10 executes the following measuring procedure:

1. Cause ultrasound energy to propagate through the sterilization chamber at each of a set of operating frequencies.
2. Measure and record the amplitude of the propagating ultrasound energy at a predetermined point in the chamber at each operating frequency.
3. Apply an analytical technique to the set of measured amplitudes and a model of the amplitude response of the system to known gas concentrations to determine the concentration of each gas in the chamber.

Figure 6:
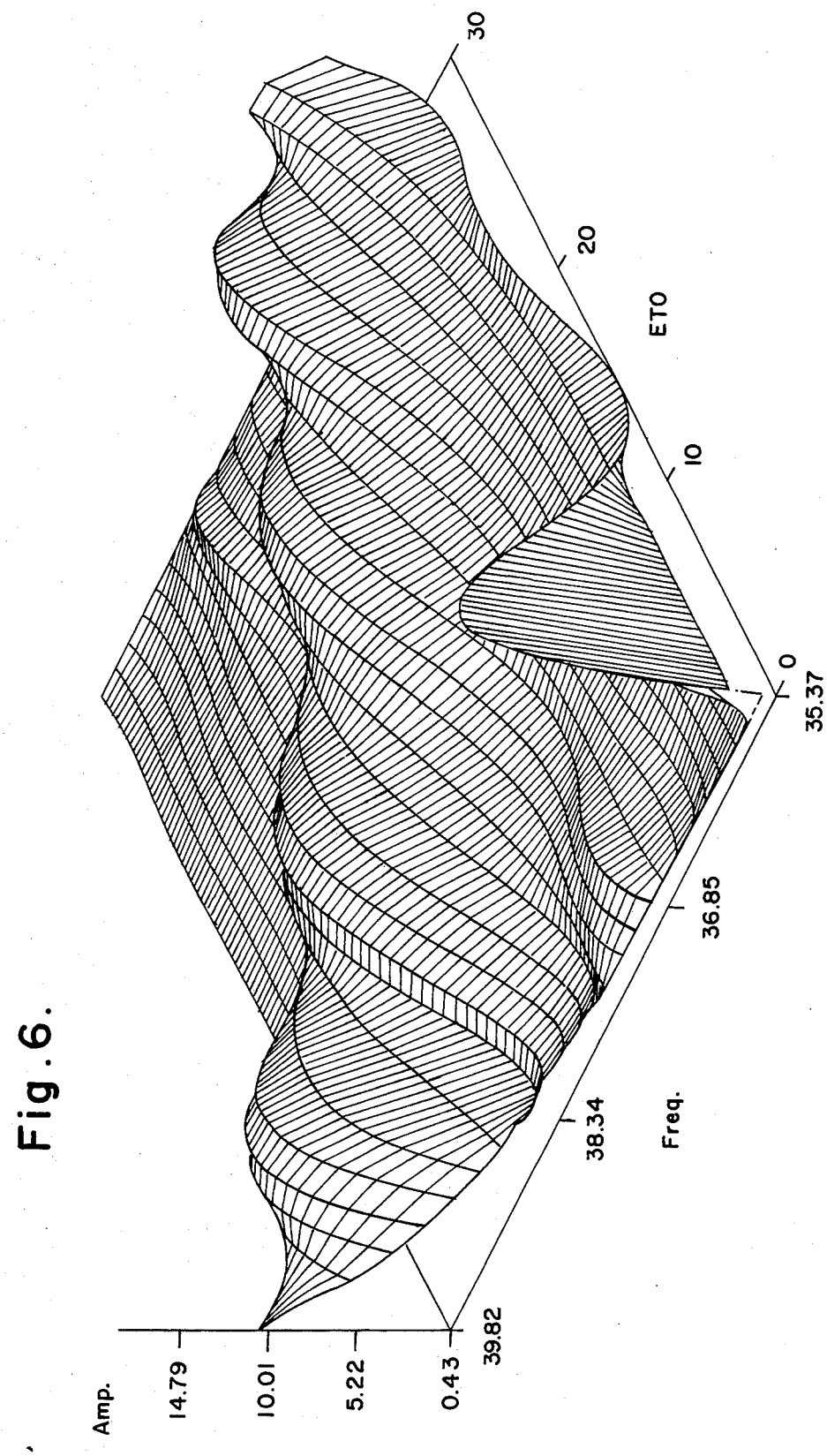
FIG. 6 is a plot of the variation of the amplitude of ultrasound propagating through a chamber containing EtO, in various concentrations, at each of a number of operating frequencies.

The amplitude response of the system is the amplitude of the ultrasound energy propagating through the gases of interest in varying concentrations through the range of operating frequencies. A typical amplitude response for EtO is shown graphically in FIG. 6.

The model of the amplitude response can be developed using any of a variety of suitable methods. Each of two particularly suitable methods employ the following test procedure:

1. Choose a set of discrete test concentrations for each gas of interest.
2. Choose a set of ultrasound operating frequencies.
3. Inject into the sterilizing chamber each gas of interest at one of the concentrations of the chosen set of concentrations.
4. Cause ultrasound to propagate through the chamber at each of the chosen set of operating frequencies and record the amplitude of the ultrasound at each operating frequency. The set of recorded amplitude values corresponding to a test concentration (if there is only one gas of interest) or a combination of test concentrations (if there is more than one gas of interest) will be referred to as a characteristic set of amplitudes.

5. Repeat steps 3 and 4 at different concentrations, or combinations of concentrations, until there is recorded a characteristic set of amplitudes for all possible concentrations or combinations of concentrations. Table I, presented below, is referred to as a test table. Table I was developed using the test procedure outlined above. The test concentrations of EtO chosen were 0%, 1%, 2%, 3%, 4%, 5% and 6%. The operating frequencies were chosen to be frequencies $f_1$, $f_2$, $f_3$, $f_4$ and $f_5$.

TABLE I

| CONCENTRATION OF EtO (%) | | | | | |
|---|---|---|---|---|---|
| 6 | 12.05 | 1.37 | 1.69 | 2.59 | 5.20 |
| 5 | 13.75 | 1.18 | 2.15 | 1.79 | 3.90 |
| 4 | 14.72 | .98 | 2.63 | 1.12 | 2.63 |
| 3 | 14.53 | .82 | 3.00 | .67 | 1.56 |
| 2 | 12.63 | .76 | 3.07 | .53 | .96 |
| 1 | 8.41 | .85 | 2.62 | .83 | 1.12 |
| 0 | 1.12 | 1.2 | 1.38 | 1.7 | 2.4 |
| | $f_1$ | $f_2$ | $f_3$ | $f_4$ | $f_5$ |
| | ULTRASOUND OPERATING FREQUENCY | | | | |

Each entry of Table I represents the amplitude of ultrasound energy of a particular operating frequency travelling through a sterilization chamber that contains EtO in a particular concentration. Each row of Table I forms a characteristic set of amplitudes that corresponds to a concentration of EtO.

Table II shows the general structure of a test table that would be completed to establish a model for the amplitude response of system 10 for two gases, EtO and air. The chosen set of test concentrations for EtO is 0%, 1%, 2%, 3% and 4%. The chosen set of test concentrations for air is 0%, 2%, 4%, 6% and 8%. The operating frequencies are chosen to be $f_1$, $f_2$, $f_3$, $f_4$ and $f_5$.

TABLE II

| CONCENTRATION OF EtO, AIR (%) | | | | | |
|---|---|---|---|---|---|
| 4.8 | | | | | |
| 4.6 | | | | | |
| 4.4 | | | | | |
| 4.2 | | | | | |
| 4.0 | | | | | |
| 3.8 | | | | | |
| 3.6 | | | | | |
| 3.4 | | | | | |
| 3.2 | | | | | |
| 3.0 | | | | | |
| 2.8 | | | | | |
| 2.6 | | | | | |
| 2.4 | | | | | |
| 2.2 | | | | | |
| 2.0 | | | | | |
| 1.8 | | | | | |
| 1.6 | | | | | |
| 1.4 | | | | | |
| 1.2 | | | | | |
| 1.0 | | | | | |
| 0.8 | | | | | |
| 0.6 | | | | | |
| 0.4 | | | | | |
| 0.2 | | | | | |
| 0.0 | | | | | |
| | $f_1$ | $f_2$ | $f_3$ | $f_4$ | $f_5$ |
| | ULTRASOUND OPERATING FREQUENCY | | | | |

Table II would be completed by evacuating the sterilization chamber, causing ultrasound to propagate through the chamber at each operating frequency and entering on the bottommost row in Table II the amplitude of the ultrasound for each operating frequency. Then, a 2% concentration of air would be injected into the chamber and the system would cause ultrasound to propagate through the chamber at each operating frequency. The amplitudes of the ultrasound at each frequency would be entered on the next row of Table II. The method would be repeated while appropriately adjusting the concentrations of EtO and air in the chamber until Table II were completed. Those skilled in the art will appreciate that the test table could be reconstructed to accommodate more than two gases and to accommodate any chosen sets of gas concentrations and operating frequencies.

The test table is used to generate a set of characteristic equations. There will be a characteristic equation for each operating frequency. Each characteristic equation will be of the following form:

$$y(f_i) = a_0 + a_1 x_1 + a_2 x_2 + \ldots + a_k x_k \quad (1)$$

The term $y(f_i)$ represents the amplitude of the ultrasound (of frequency $f_i$) travelling through the chamber. Each $x_i$ can represent a particular gas concentration (for example $x_1$ could represent the concentration of EtO), a higher order gas concentration (for example, $x_2$ could represent the concentration of EtO taken to the third power), or any combination of gas concentrations (for example, $x_6$ could represent $x_1 x_3 x_4^2$, where $x_1$ is the concentration of EtO, $x_3$ is the concentration of Freon, and $x_4$ is the concentration of air). The particular form of equation (1) used will depend on the desired accuracy of the system and will be easily chosen by those of ordinary skill in the art. The coefficients, $a_i$, of each characteristic equation are determined by solving the following normal equations simultaneously:

$$Na_0 + a_1 \Sigma x_1 + a_2 \Sigma x_2 = \ldots + a_k \Sigma x_k = \Sigma y \quad (2)$$

$$a_0 \Sigma x_1 + a_1 \Sigma x_1^2 + a_2 \Sigma x_1 x_2 + \ldots + a_k \Sigma x_1 x_k = \Sigma x_1 y \quad (3)$$

$$a_0 \Sigma x_2 + a_1 \Sigma x_1 x_2 + a_2 \Sigma x_2^2 + \ldots + a_k \Sigma x_2 x_k = \Sigma x_2 y \quad (4)$$

$$a_0 \Sigma x_k + a_1 \Sigma x_k x_1 + a_2 \Sigma x_k x_2 + \ldots + a_k \Sigma x_k^2 + \Sigma x_k y \quad (5)$$

where N represents the number of ordered pairs, $x_i$, y.

Either the set of characteristic equations or a refined table, which is derived from the test table and the characteristic equations, can be used as the model of the amplitude response.

Use of the characteristic equations permits determining gas concentration at any desired resolution.

The refined table is a refinement of the test table that permits improving the resolution of the system to permit the system to determine gas concentrations other than those of the set of test concentrations. Sets of amplitudes corresponding to gas concentrations other than the test concentrations could be developed using the set of characteristic equations. For example, a row could be added to Table I to provide a set of amplitudes for a concentration of EtO of 0.5% by solving each characteristic equation for $y(f_i)$ using the known values of $a_i$ and the known concentration of EtO of 0.5.

Regardless of whether the set of characteristic equations or the refined table is used as the mathematical model, the preferred system performs the following procedure to determine gas concentration:

1. Cause ultrasound to propagate through the sterilization chamber at each operating frequency.

2. Measure the amplitude of the ultrasound at a predetermined point within the chamber at each operating frequency.

If the set of characteristic equations is used as the model, the measured amplitudes are substituted for $y(f_i)$ in each characteristic equation, and the set of equations is solved using Cramer's rule. If the refined table is employed as the model, the measured amplitudes are compared to each characteristic set of amplitudes stored in the table. Any suitable criteria can be used to determine to which characteristic set the measured amplitudes most closely fit. One suitable approach requires determining for each characteristic set the number of members of the characteristic set that deviate from the corresponding member of the measured set by less than a predetermined value. The concentration corresponding to the characteristic set having the greatest number of matches to the measured set of amplitudes is deemed to be the concentration of the gases present in the chamber. For example, measured amplitudes of 14.5, 0.8, 3.0, 0.6 and 1.6 would most closely match the characteristic set of amplitudes of Table I corresponding to a 3% concentration of EtO.

SYSTEM

Figure 1:
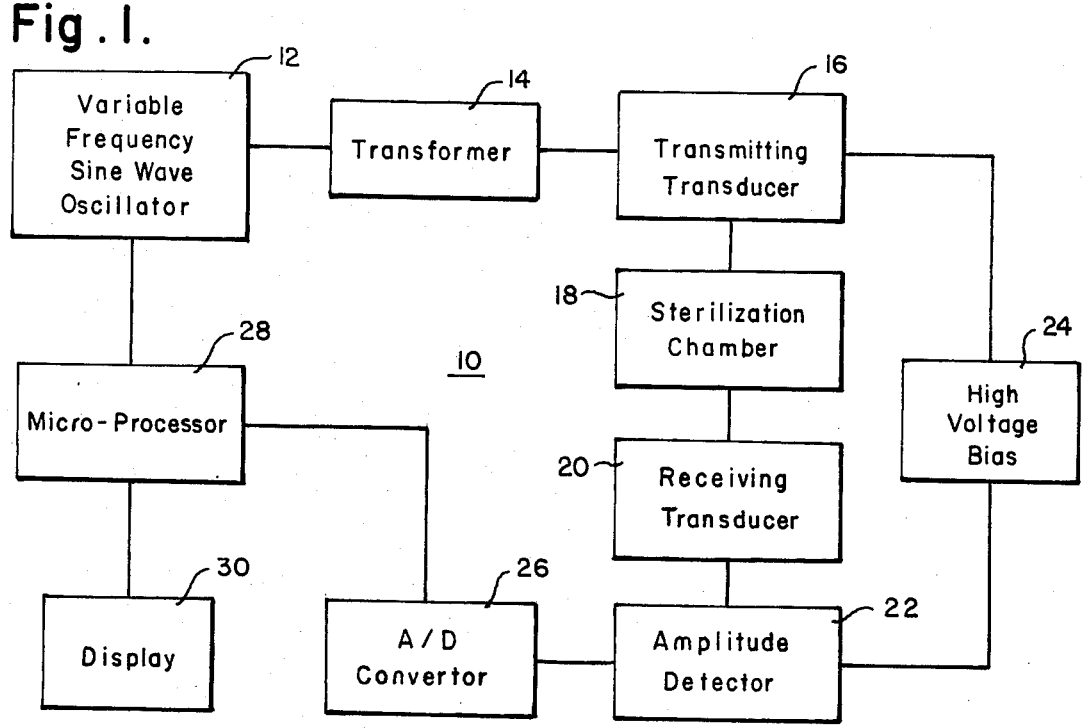
FIG. 1 is a block diagram of a preferred system constructed according to the provisions of the present invention.

FIG. 1 shows preferred system 10. A variable frequency sine wave oscillator 12 produces a 15 volt sinusoidal electrical signal that is increased to 100 volts by a broad band transformer 14. Transmitting transducer 16 receives the 100 volt sinusoidal signal from transformer 14 and produces ultrasound at the frequency of the received sinusoidal signal. The ultrasound energy produced by transducer 16 is directed through sterilization chamber 18 and is received by receiving transducer 20. Receiving transducer 20 converts the ultrasound signal to an electrical signal having an amplitude that is proportional to the amplitude of the ultrasound signal and a frequency equal to that of the ultrasound signal. High voltage bias 24 produces the 320 volt signal that must be maintained on transducers 16 and 20 to permit them to operate properly. Amplitude detector 22 receives the electrical signal from transducer 20 and produces an output that is proportional to the peak amplitude of each cycle of the signal produced by transducer 20. A/D converter 26 receives the signal produced by amplitude detector 22 and converts it to a digital signal which it provides to microprocessor 28.

Microprocessor 28 can be any suitable general purpose microprocessor. Microprocessor 28 is suitably programmed to operate the system as described in the section above entitled "Methodology". Among the tasks microprocessor 28 must perform are the following:

1. Coordinate the operation of system 10.
2. Store the model of the amplitude response of system 10—the microprocessor 28 must store either the refined table (of the type shown in Tables I and II) or the set of characteristic equations.
3. Store the set of operating frequencies.
4. Cause oscillator 12 to repetitively produce a sinusoidal electrical signal at each operating frequency.
5. Store the digital signal produced by A/D converter 26 for each operating frequency.
6. Either (i) substitute for $y(f_i)$ the measured amplitude values (the digital signals received from A/D converter 26) and solve the resulting set of simultaneous characteristic equations using Cramer's rule and display the calculated gas concentrations, or (ii) apply the selected set of criteria against the measured amplitude values and the refined table to determine which characteristic set of amplitudes most closely matches the measured amplitudes, and display the gas concentration corresponding to the chosen characteristic set.

Figure 2:
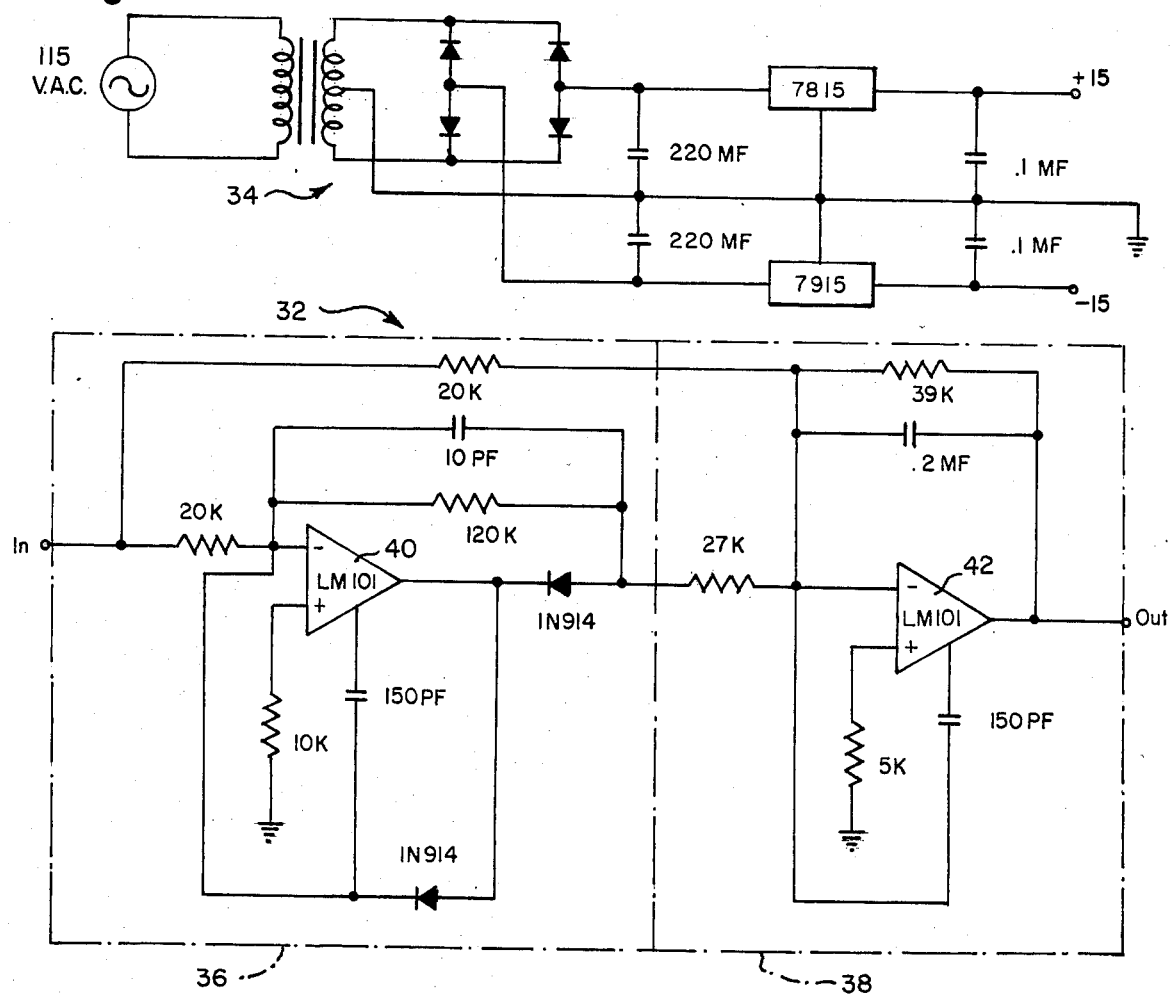
FIG. 2 is a circuit diagram of a specific amplitude detector that can be used to implement the amplitude detector depicted in FIG. 1.

FIG. 2 shows a circuit 32 that is particularly suitable for implementing the amplitude detector 22 shown in FIG. 1. Circuit 32 includes a power supply 34, a precision rectifier 36 and a low pass filter 38. Power supply 34 produces the positive and negative 15 volt control power used by differential amplifiers 40 and 42. Low pass filter 38 produces at the OUT terminal the peak amplitude of each cycle of the electrical signal received from transducer 20 at the IN terminal. The specific details of the construction and operation of circuits 34, 36 and 38 are obvious and, hence, a further description of those circuits will not be provided.

A description of the method performed by system 10 follows:

1. Microprocessor 28 causes oscillator 12 to produce a sinusoidal electrical signal of a frequency equal to the first operating frequency.
2. Transducer 16 causes an ultrasound signal of a frequency equal to that of the signal produced by oscillator 12 to propagate through the sterilization chamber.
3. Transducer 20 produces a sinusoidal signal of a frequency equal to that of the ultrasound signal received by it. Amplitude detector 22 determines the peak amplitude of the signal produced by transducer 20.
4. A/D converter 26 converts the analog signal received from detector 22 to a digital signal.
5. Microprocessor 28 receives the digital signal produced by converter 26 and stores it as the amplitude corresponding to the first operating frequency.
6. Steps 1 through 5 are repeated for each operating frequency until microprocessor 28 has stored a measured amplitude for each operating frequency.
7. Microprocessor 28 employs the stored set of measured amplitudes and either the refined table of amplitudes stored in its memory or the set of characteristic equations representing the amplitude response of system 10 to calculate and display the concentration of each gas present within the sterilizer.

What is claimed is:

1. A system that provides an indication of the concentration of at least one gas present within a chamber comprising:

means for causing mechanical radiant energy to propagate through the chamber at at least two operating frequencies which provide unique information over at least a portion of various gas concentrations;

means for measuring the amplitude of said propagating mechanical radiant energy at each operating frequency at a predetermined point within the chamber; and means for fitting said measured amplitudes to a modeled amplitude response representative of a plurality of concentrations of the at least one gas to determine the concentration of the at least one gas present in the chamber.

2. The system of claim 1 wherein said means for fitting includes a means for storing a table of test data and means for comparing said measured amplitudes to said table of test data.

3. The system of claim 1 wherein said means for fitting includes means for simultaneously solving a set of characteristic equations.

* * * * *

UNITED STATES PATENT AND TRADEMARK OFFICE
CERTIFICATE OF CORRECTION

PATENT NO. : 4,616,501
DATED : October 14, 1986
INVENTOR(S) : Douglas M. Mechlenburg It is certified that error appears in the above—identified patent and that said Letters Patent is hereby corrected as shown below:

Col. 3, line 15, delete "2.63" second occurrence and substitute therefor --2.62--; and Col. 3, lines 59 and 60, delete in their entirety and substitute therefor

--0.0

| $f_1$ | $f_2$ | $f_3$ | $f_4$ | $f_5$ |
|---|---|---|---|---|

--.

Signed and Sealed this

Twenty-third Day of December, 1986

Attest:

DONALD J. QUIGG

Attesting Officer     Commissioner of Patents and Trademarks